(12) United States Patent
Hancock et al.

(10) Patent No.: US 12,011,219 B2
(45) Date of Patent: Jun. 18, 2024

(54) ELECTROSURGICAL INSTRUMENT

(71) Applicant: CREO MEDICAL LIMITED, Chepstow (GB)

(72) Inventors: Christopher Paul Hancock, Bath (GB); Patrick Burn, Chepstow (GB); Pallav Shah, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 681 days.

(21) Appl. No.: 17/058,541

(22) PCT Filed: May 24, 2019

(86) PCT No.: PCT/EP2019/063489
§ 371 (c)(1),
(2) Date: Nov. 24, 2020

(87) PCT Pub. No.: WO2019/228928
PCT Pub. Date: Dec. 5, 2019

(65) Prior Publication Data
US 2021/0196377 A1 Jul. 1, 2021

(30) Foreign Application Priority Data
May 30, 2018 (GB) ...................... 1808806

(51) Int. Cl.
*A61B 18/18* (2006.01)
*A61B 1/018* (2006.01)
(Continued)

(52) U.S. Cl.
CPC .......... *A61B 18/1815* (2013.01); *A61B 1/018* (2013.01); *A61B 18/1492* (2013.01);
(Continued)

(58) Field of Classification Search
CPC ..... A61B 1/018; A61B 18/1492; A61B 18/16; A61B 18/1815; A61B 2018/00083;
(Continued)

(56) References Cited

U.S. PATENT DOCUMENTS

2010/0125269 A1  5/2010  Emmons et al.
2011/0213351 A1*  9/2011  Lee .................... A61B 18/1815
606/41

(Continued)

FOREIGN PATENT DOCUMENTS

EP  2361581 A1  8/2011
EP  2869778 A1  5/2015
(Continued)

OTHER PUBLICATIONS

International Preliminary Report of Patentability issued by the International Preliminary Examining Authority corresponding to International Patent Application No. PCT/EP/2019/063489, dated Oct. 14, 2020.

(Continued)

Primary Examiner — Khadijeh A Vahdat
(74) Attorney, Agent, or Firm — ArentFox Schiff LLP (57) ABSTRACT

An electrode structure for a distal tip of an electrosurgical instrument that enables efficient delivery of radiofrequency (RF) energy in a forward (distal) direction and uniform delivery of microwave energy for ablation in a region surrounding the distal tip. The instrument comprises a tip body having a first electrode and a second electrode, where the second electrode is spaced from the first electrode exposed dielectric material. The first electrode is connected through the tip body to an inner conductor of a coaxial feed. The second electrode is electrically connected to the outer conductor of the coaxial feed by a field-shaping conductive structure formed in or on the tip body. The field-shaping conductive structure is configured to shape a radiation profile of microwave energy emitted from the tip body.

22 Claims, 8 Drawing Sheets

(51) Int. Cl.
*A61B 18/14* (2006.01)
*A61B 18/16* (2006.01)
*A61B 18/00* (2006.01)

(52) U.S. Cl.
CPC .... *A61B 18/16* (2013.01); *A61B 2018/00541* (2013.01); *A61B 2018/00577* (2013.01); *A61B 2018/00601* (2013.01); *A61B 2018/00982* (2013.01); *A61B 2018/00994* (2013.01); *A61B 2018/1861* (2013.01)

(58) Field of Classification Search
CPC ........... A61B 2018/00541; A61B 2018/00577; A61B 2018/00601; A61B 2018/00982; A61B 2018/00994; A61B 2018/1273; A61B 2018/1846; A61B 2018/1861
See application file for complete search history.

(56) References Cited

U.S. PATENT DOCUMENTS

| | | |
|---|---|---|
| 2015/0196350 A1 | 7/2015 | Carmel et al. |
| 2015/0313670 A1 | 11/2015 | Shroff et al. |
| 2017/0215955 A1 | 8/2017 | Hancock et al. |

FOREIGN PATENT DOCUMENTS

| | | |
|---|---|---|
| GB | 2486343 A | 6/2012 |
| GB | 2487199 A | 7/2012 |
| GB | 2532345 A | 5/2016 |
| GB | 2550414 A | 11/2017 |
| WO | WO 2010/048335 A1 | 4/2010 |
| WO | WO 2017/008020 A1 | 1/2017 |
| WO | WO 2017/149072 A2 | 9/2017 |
| WO | WO 2017174513 A1 | 10/2017 |
| WO | WO 2017/202737 A1 | 11/2017 |

OTHER PUBLICATIONS

International Search Report issued by the International Searching Authority in corresponding International Patent Application No. PCT/EP2019/063489, dated Jul. 5, 2019.

Search Report issued by the British Patent Office in corresponding British Patent Application No. 1808806.2, dated Nov. 21, 2018.

Written Opinion issued by the International Preliminary Examining Authority corresponding to International Patent Application No. PCT/EP2019/063489, dated Apr. 4, 2020.

* cited by examiner

ELECTROSURGICAL INSTRUMENT

CROSS-REFERENCE TO RELATED APPLICATIONS

This application is a National Stage entry of International Application No. PCT/EP2019/063489, filed on May 24, 2019, which claims priority to British Patent Application No. 1808806.2, filed on May 30, 2018. The disclosures of the priority applications are hereby incorporated in their entirety by reference.

FIELD OF THE INVENTION

The invention relates to an electrosurgical instrument for delivering microwave energy and/or radiofrequency energy to biological tissue in order to ablate the target tissue. The probe may be inserted through a channel of an endoscope or catheter, or may be used in percutaneous surgery, laparoscopic surgery or open surgery.

BACKGROUND TO THE INVENTION

Electromagnetic (EM) energy, and in particular microwave and radiofrequency (RF) energy, has been found to be useful in electrosurgical operations, for its ability to cut, coagulate, and ablate body tissue. Typically, apparatus for delivering EM energy to body tissue includes a generator comprising a source of EM energy, and an electrosurgical instrument connected to the generator, for delivering the energy to tissue. Conventional electrosurgical instruments are often designed to be inserted percutaneously into the patient's body. However, it can be difficult to locate the instrument percutaneously in the body, for example if the target site is in a moving lung. Other electrosurgical instruments can be delivered to a target site by a surgical scoping device (e.g. an endoscope) which can be run through channels in the body such as airways. This allows for minimally invasive treatments, which can reduce the mortality rate of patients and reduce intraoperative and postoperative complication rates.

Tissue ablation using microwave EM energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating.

This principle is harnessed in microwave ablation therapies, where water molecules in target tissue are rapidly heated by application of a localised electromagnetic field at microwave frequencies, resulting in tissue coagulation and cell death. It is known to use microwave emitting probes to treat various conditions in the lungs and other organs. For example, in the lungs, microwave radiation can be used to treat asthma and ablate tumours or lesions.

RF EM energy can be used for cutting and/or coagulation of biological tissue. The method of cutting using RF energy operates based on the principle that as an electric current passes through a tissue matrix (aided by the ionic contents of the cells), the impedance to the flow of electrons across the tissue generates heat. When a pure sine wave is applied to the tissue matrix, enough heat is generated within the cells to vaporise the water content of the tissue. There is thus a large rise in the internal pressure of the cell that cannot be controlled by the cell membrane, resulting in the cell rupturing. When this occurs over a wide area it can be seen that tissue has been transected.

RF coagulation operates by applying a different waveform to the tissue, whereby instead of being vaporised, the cell contents are heated to around 65° C. This dries out the tissue by desiccation and also denatures the proteins.

SUMMARY OF THE INVENTION

At its most general, the invention provides an electrode structure for a distal tip of an electrosurgical instrument that enables both efficient delivery for radiofrequency (RF) energy in a forward (distal) direction and uniform delivery of microwave energy for ablation in a region surrounding the distal tip. The RF energy can be delivered in a focussed way, e.g. so that the RF energy operates to cut tissue accurately to facilitate positioning of the distal tip. In contrast, the microwave energy may be delivered more broadly, e.g. in an omnidirectional manner, to facilitate effective ablation.

By inserting the radiating tip portion into the target tissue before delivering the microwave energy, it is possible to increase the efficiency with which the microwave energy is delivered to the target tissue, whilst minimising the amount of microwave energy delivered to healthy tissue. The electrosurgical instrument may be used to apply RF and microwave energy simultaneously or separately, e.g. one after the other.

Typically, different tools are used for cutting into the outer wall of a tumour and ablating the tumour. The inventors have realised that because of this, there is a risk of seeding cancerous cells in healthy parts of the body when the tool for cutting into the tumour is withdrawn from the body. In the present invention, a single electrosurgical instrument is used for both cutting and ablating tissue, so there may be a reduced risk of seeding cancerous cells in healthy areas of the body. A further advantage of the electrosurgical instrument of the invention is that less time may be spent on interchanging instruments during a surgical procedure. In particular, the present invention enables a rapid change in functionality of the instrument between RF cutting and microwave ablation.

According to a first aspect of the invention, there is provided an electrosurgical instrument comprising: a coaxial feed cable for conveying microwave energy and radiofrequency energy, the coaxial feed cable having an inner conductor, an outer conductor, and a first dielectric material separating the inner conductor and the outer conductor; and a radiating tip portion disposed at a distal end of the coaxial cable to receive the microwave energy and the radiofrequency energy, the radiating tip portion comprising: a tip body made of a second dielectric material, the tip body having a proximal end that is connected to a distal end of the coaxial feed cable and a distal end facing away from the coaxial feed cable; and a first electrode and a second electrode disposed on the distal end of the tip body, the second electrode being spaced from the first electrode by a portion of exposed second dielectric material, wherein the first electrode is electrically connected to the inner conductor of the coaxial feed cable by a conductive element that extends through the tip body, wherein the second electrode is electrically connected to the outer conductor of the coaxial cable by a field-shaping conductive structure formed in or on the tip body, wherein the first electrode and second electrode are configured as active and return electrodes for delivering the radiofrequency energy, wherein the conductive element and the field-shaping conductive structure are configured as an antenna for emitting the microwave energy, and wherein the field-shaping conductive structure is configured to shape a radiation profile of microwave energy emitted from the radiating tip portion.

With this structure, the instrument can cut and ablate target tissue in the body. The instrument may be particularly suited to the ablation of tissue in the lungs, however it may be used to ablate tissue in other organs including but not limited to liver, kidney and muscle. In order to efficiently ablate target tissue, it is desirable for the radiating tip portion to be located as close as possible (and in many cases inside) the target tissue. In order to reach the target tissue (e.g. in the lungs), the instrument may need to be guided through passageways (e.g. airways) and around obstacles. This means that the instrument will ideally be flexible and have a small cross section. Particularly, the device should be very flexible near its tip, where it may need to be steered along passageways such as bronchioles which can be narrow and winding.

The coaxial feed cable may be a conventional coaxial cable that is connectable at one end to an electrosurgical generator. In particular, the inner conductor may be an elongate conductor extending along a longitudinal axis of the coaxial feed cable. The first dielectric material may be disposed around the inner conductor, e.g. the first dielectric material may have a channel through which the inner conductor extends. The outer conductor may be a sleeve made of conductive material that is disposed on the surface of the first dielectric material. The coaxial feed cable may further include an outer protective sheath for insulating and protecting the cable. In some examples, the protective sheath may be made of or coated with a non-stick material to prevent tissue from sticking to the cable. The radiating tip portion is located at the distal end of the coaxial feed cable. The radiating tip portion may be permanently attached to the coaxial feed cable, or it may be removably attached to the coaxial feed cable. For example, a connector may be provided at the distal end of the coaxial feed cable, which is arranged to receive the radiating tip portion and form the required electrical connections.

The tip body serves as a support for the first and second electrodes and the field-shaping conductive structure. The second dielectric material may be the same as, or different from, the first dielectric material. The second dielectric material may be selected to improve impedance matching with target tissue in order to improve the efficiency with which the microwave energy is delivered into target tissue. In some examples, the tip body may be made of multiple different dielectric materials, which are selected and arranged to shape the microwave emission profile in a desired manner. In examples where the first and second dielectric materials are the same, the tip body may be formed by a portion of the first dielectric material that protrudes beyond the distal end of the coaxial feed cable. This may simplify construction of the radiating tip portion, and avoid reflections of EM energy at the boundary between the radiating tip portion and the coaxial feed cable.

The first and second electrodes are disposed on the tip body, i.e. they are exposed on a surface of the tip body. The first and second electrodes are electrically connected to the inner conductor and outer conductor of the coaxial feed cable, respectively. Thus, the first and second electrodes can receive radiofrequency energy conveyed along the coaxial feed cable and so can be used as bipolar RF cutting electrodes. By conveying radiofrequency energy to the first and second electrodes, biological tissue that is located between the electrodes may be cut and/or coagulated via the mechanisms discussed above.

The tip body may include a channel through which a conductive element extends to electrically connect the first electrode to the inner conductor. The channel may be a tunnel-like passage through a portion of the tip body. Thus, a portion of the conductive element may be surrounded by the tip body. A cross-section of the channel may match a cross-section of the conductive element, such that the conductive element is in contact with the tip body in the channel. Additionally or alternatively, the conductive element may be secured inside the channel using an adhesive or epoxy. As explained below, the conductive element may be a distally protruding portion of the inner conductor.

The field-shaping conductive structure serves to connect the second electrode to the outer conductor of the coaxial feed cable. The field-shaping conductive structure is isolated from the first conductor by the second dielectric material of the tip body. Thus, there may be a thickness of second dielectric material between the conductive element and the field-shaping conductive structure. The field-shaping conductive structure and conductive element may be arranged coaxially, with the second dielectric formed therebetween.

Together, the conductive element and the field-shaping conductive structure are configured as an antenna for emitting microwave energy. The field-shaping conductive structure serves to shape the radiation profile of emitted microwave energy. For example, if it is desired to preferentially emit microwave energy in a particular direction, the field-shaping conductive structure may be a piece of conductive material arranged on a side of the tip body, to block microwave energy from being emitted from that side of the radiating tip portion. More complex radiation profiles may be obtained by appropriately shaping and positioning the field-shaping conductive structure.

The configuration of the radiating tip portion therefore enables treatment of tissue using both RF and microwave energy. In particular, the field-shaping conductive structure enables emission of microwave energy from the radiating tip portion whilst maintaining electrical connection to the second electrode, to enable RF cutting between the first and second electrodes.

In some embodiments, the field-shaping conductive structure may include an elongate conductor extending along a length of the radiating tip portion. For example, the field-shaping conductive structure may be a wire or strip of conductive material connecting the outer conductor to the second electrode. The elongate conductor may be parallel to the longitudinal direction of the electrosurgical instrument. The elongate conductor may act to partially block emission of microwave energy, such that the radiation profile is asymmetric about the longitudinal axis of the instrument. This may enable microwave energy to be emitted from a side of the radiating tip portion, to provide directional microwave ablation.

In some embodiments, the field-shaping conductive structure may include a slotted conductive structure formed around the conductive element. For example, the slotted conductive structure may be a conductive sleeve having a slot formed in the sleeve. In another example, the conductive structure may be formed by a helical conductive element that is wound around the tip body. In this example, the slot is a helical slot formed by a gap between adjacent windings.

The slot in the conductive structure enables microwave energy to escape from the radiating tip portion. The slot may be an opening or gap in the conductive material making up the slotted conductive structure. The rest of the conductive structure (i.e. the conductive material making up the conductive structure) may act to block microwave energy from escaping from the radiating tip portion. As microwave energy is conveyed along the radiating tip portion of the instrument, the microwave energy may be emitted through the slot. In particular, the slot may interrupt field lines running along the outer conductor and the conductive structure, causing the slot to radiate microwave energy. The first conductor and the slotted conductive structure may therefore act as a slotted (or "leaky") microwave antenna. The dimensions and shape of the slot may be arranged to obtain a desired microwave radiation profile. For example, if it is desired to emit microwave energy only from one side of the radiating tip portion, the slot may be placed on the corresponding side of the conductive structure. A width of the slot may be shorter than or equivalent to the wavelength of the microwave energy, to ensure efficient emission of the microwave energy from the slot. The electrical length of the slot may be adjusted by using a loaded dielectric material (i.e. having permittivity>1) in the tip body.

In some embodiments, the slotted conductive structure may comprise a helical conductive element wound around the outer surface of the tip body to form a helical slot in which the second dielectric material is exposed. The helical slot may enable microwave energy to be emitted from the radiating tip portion substantially symmetrically about the longitudinal axis of the electrosurgical instrument. This may enable tissue to be ablated in a well-defined volume that surrounds the radiating tip portion. The helical slot may extend from a proximal end of the tip body to a distal end of the tip body, so that microwave energy can be radiated around the whole length of the tip body. The helical slot may be formed by winding or depositing a conductive material around the tip body to form a helix-shaped conductor or by cutting out or etching the helical slot from a conductive sleeve.

As a result of having a helical slot in the conductive structure, the conductive structure includes a helical conductor that provides an electrical path between the second electrode and the outer conductor. A width of the helical slot may be shorter than or equivalent to, the wavelength of the microwave energy, to enable efficient emission of the microwave energy.

In some embodiments, the pitch of the helical slot may vary along a length of the conductive structure. Herein, the pitch of the helical slot refers to the length in the longitudinal direction corresponding to one complete turn in the helix. The "length" of the conductive structure refers to a length in the longitudinal direction of the electrosurgical instrument. In one example, the pitch of the helical slot may increase from a proximal end of the conductive structure to a distal end of the conductive structure. In other words, the spacing between adjacent turns in the helical slot may increase towards the distal end of the conductive structure. In an alternative example, the pitch of the helical slot may decrease from the proximal end of the conductive structure to the distal end of the conductive structure, i.e. the spacing between adjacent turns decreases towards the distal end. Varying the pitch of the helical slot along the length of the conductive structure may enable the radiation profile of the microwave energy to be adjusted. For example, by increasing the pitch of the helical slot near the distal end, more microwave energy may be radiated from the distal end of the radiating tip portion. In particular, the helical slot determines the location of microwave emission (from gaps in the conductive structure). By changing the pitch, the location/position of the gaps is changed with respect to the radiating tip portion. This may result in a change to the radiation profile.

In some embodiments, the helical slot may be tapered along a length of the conductive structure. In other words, the width of the helical slot may be varied (e.g. increased or decreased) along the length of the conductive structure. This may be achieved, for example, by varying a width of the helical conductor along the length of the conductive structure. Similar to changing the pitch of the helical conductor, varying the width of the helical conductor may serve to shape the microwave radiation profile of the radiating tip portion in a desired manner. As energy is radiated from the proximal end of the radiating tip portion, there is less energy remaining to travel down the length of the radiating tip portion. By increasing the width of the helical slot towards the distal end of the radiating tip portion, a larger proportion of the remaining energy is able to propagate/couple into the surrounding tissue. This may serve to provide a more uniform ablation profile along the length of the radiating tip portion. In other words, at the proximal end of the radiating tip portion, a small proportion of a large amount of energy may be radiated, whilst at the distal end a large proportion of a small amount of energy may be radiated.

In some embodiments, a width of the slot of the conductive structure may be around a tenth of a wavelength of the microwave energy in the biological tissue. This may serve to balance the amount of energy radiated/coupled into surrounding tissue along the length of the radiating tip portion.

In some embodiments, the slotted conductive structure may include a plurality of slots for emitting the microwave energy. Thus, microwave energy may be emitted from each of the plurality of slots. For example, by placing the slots in different areas of the slotted conductive structure, microwave energy may be emitted from different parts of the radiating tip portion. Additionally, interference between the microwave energy emitted at each of the plurality of slots may affect the radiation profile, such that highly directional emission of microwave energy may be achieved.

In some embodiments, each of the plurality of slots may have an identical width, and the slots may be evenly spaced along a longitudinal direction of the radiating tip portion. In other words, the plurality of slots may be arranged in a periodic array along the longitudinal direction of the radiating tip portion. This arrangement of the slots may result in a resonance of the microwave energy in the radiating tip portion. As the microwave energy travels down the radiating tip portion, microwave energy may be radiated from the slots. At the distal end of the radiating tip portion, a partial reflection of the microwave energy may occur. The reflected microwave energy may be radiated from the slots as it travels back up the radiating tip portion. Such a reflective cycle may be repeated inside the radiating tip portion. Thus, the radiating tip portion may behave as a resonant microwave antenna.

In some embodiments, each of the plurality of slots may have a different width, and the plurality of slots may be arranged along a longitudinal direction of the radiating tip portion in order of increasing or decreasing width. Thus, the width of the slots may increase or decrease from the proximal end of the radiating tip portion to its distal end. Preferably, the slot with the smallest width may be located at the proximal end, and the slot with the largest width may be located at the distal end. This arrangement of the slots may enable the radiating tip portion to behave as a traveling wave microwave antenna. This is because this arrangement of the slots may result in a positive gradient of coupling efficiency from within the radiating tip portion to the surrounding tissue.

In some embodiments, the slotted conductive structure may be disposed on an outer surface of the tip body. Thus, the outer surface of the tip body may serve as a support for the slotted conductive structure. For example, the slotted conductive structure may be adhered or otherwise secured to the outer surface of the tip body. This may facilitate construction of the radiating tip portion. This may also improve the isolation between the first conductor and the conductive structure, as the first conductor passes through the channel inside the tip body whilst the conductive structure is on the outside of the tip body. The radiating tip portion may further include a protective layer (e.g. made of an insulating material) disposed over the slotted conductive structure to protect the slotted conductive structure from its surroundings. However, in alternative embodiments, the slotted conductive structure may be partially embedded in the tip body, e.g. the slotted conductive structure may be disposed below an outer surface of the tip body. In this manner, the outer surface of the tip body may act to protect the slotted conductive structure.

In some embodiments, the conductive element comprises a distal portion of inner conductor that protrudes through the tip body to connect to the first electrode. In other words, the conductive element may be a continuation of the inner conductor that extends beyond the distal end of the coaxial feed cable and passes through the channel in the tip body. This avoids having to form an electrical connection between the conductive element and the inner conductor at the interface between the radiating tip portion and the coaxial feed cable. This may improve reliability of the electrical connection to the first electrode. This may also simplify construction of the radiating tip portion, as it can be made at the end of a coaxial feed cable using the inner conductor of the coaxial feed cable.

In some embodiments, the first electrode may be formed by an exposed distal tip of the inner conductor. In other words, the inner conductor may extend through the channel in the tip body so that the distal tip of the inner conductor is exposed through an opening in the channel. For example, the channel may have an opening at the distal end of the tip body, where the distal tip of the inner conductor is exposed. The distal tip of the inner conductor may protrude from the channel, e.g. it may extend beyond the distal end of the tip body. Alternatively, the distal tip of the inner conductor may lie flush with the tip body, so that it does not protrude beyond the distal end of the tip body. This may avoid sharp edges around the distal tip of the inner conductor, which could catch on tissue. By using the distal tip of the inner conductor as the first electrode, construction of the radiating tip portion may be simplified. This is because the inner conductor acts as both the first conductor and the first electrode, so the number of components and the number of electrical connections required for making the radiating tip portion can be reduced.

In some embodiments, the conductive structure may be formed by an extension of the outer conductor over the tip body. In other words, the outer conductor may run continuously from the coaxial feed cable to the radiating tip portion without any interruptions. For example, the outer conductor may form a sleeve that passes over the tip body. The slot may be formed in the portion of the outer conductor that extends over the tip body. This may facilitate forming the radiating tip portion at the end of the coaxial feed cable, as the outer conductor provides a conductive structure in which a slot can easily be cut. It also avoids the need of attaching and electrically connecting a separate conductive structure at the distal end of the coaxial feed cable.

In some embodiments, the slotted conductive structure may be electrically connected to the outer conductor by a conductive ring disposed at the distal end of the coaxial feed cable. One side of the conductive ring may be electrically connected to the outer conductor (e.g. soldered or welded), and the other side of the conductive ring may be electrically connected to the conductive structure. The conductive ring may provide a large surface to which electrical connection can be made, to facilitate electrical connection to the outer conductor and improve reliability of the connection. The conductive ring may be made of a rigid material to further facilitate electrical connection to the outer conductor (which may made be made of a flexible material for flexibility of the coaxial feed cable). The conductive ring may also serve to shape the microwave radiation profile of the radiating tip portion, as it provides an area of conductive material connected to the outer conductor.

In some embodiments, the tip body may include an end face at a distal end of the tip body, and the first electrode and the second electrode may be disposed on the end face of the second dielectric material. The end face may be a planar surface on which the first and second electrode are disposed. Biological tissue that is adjacent to the end face of the tip body may thus be cut using RF energy. The end face may be oriented in a particular direction, to obtain a desired cut direction. Cutting tissue at the distal end of the tip body may facilitate tunnelling of the radiating tip portion into target tissue, so that microwave energy can be efficiently delivered to the target tissue.

In some embodiments, the end face may lie in a plane that is normal to a longitudinal axis of the coaxial feed cable. Thus, the end face of the tip body may face forwards, i.e. away from the coaxial feed cable. This configuration may enable biological tissue that is located directly in front of the radiating tip portion to be cut using RF energy delivered to the first and second electrodes. This may facilitate tunnelling of the instrument into target tissue. For example, tunnelling into target tissue may be achieved by cutting tissue in front of the instrument using RF energy and pushing the instrument forwards through the cut tissue until a target zone is reached.

In some embodiments, the second electrode may be a conductive ring that surrounds the first electrode. In other words, second electrode may be a loop of conductive material disposed around the first electrode. This may enable tissue to be cut in a region around the first electrode, the region being defined by the shape of the second electrode. This may shape the cut in the tissue in a manner that facilitates tunnelling of the radiating tip portion into target tissue.

In some embodiments, an outer diameter of the second electrode may be substantially the same as an outer diameter of the tip body. This may enable a cut made with the first and second electrodes to have approximately the same size as the tip body, so that the radiating tip portion can be easily pushed through the cut tissue. Additionally, shape of the conductive ring may approximately match a cross-section of the tip body, to further facilitate tunnelling of the radiating tip portion into cut tissue. For example, where the tip body has a circular cross-section, the second electrode may be a circular ring having an outer diameter that matches the outer diameter of the tip body.

In some embodiments, the tip body may be cylindrical, a longitudinal axis of the tip body being aligned with a longitudinal axis of the coaxial feed cable. Thus, the tip body may have a circular cross-section, facilitating insertion of the electrosurgical instrument through the working channel of a surgical scoping device. The cylindrical shape of the tip body may also provide a convenient end face on which the first and second electrodes can be disposed for cutting tissue in front of the radiating tip portion.

In some embodiments, an outer diameter of the cylindrical tip body may be substantially the same as an outer diameter of the coaxial feed cable. The tip body and the coaxial feed cable may therefore have cross-sections that are approximately the same. In this manner, the tip body may appear as an extension of the coaxial feed cable. As a result, the electrosurgical instrument may have a substantially constant outer diameter along its whole length. This may further facilitate use of the electrosurgical instrument in a surgical scoping device, as well as tunnelling of the instrument into target tissue.

The electrosurgical instrument discussed above may form part of a complete electrosurgical system. For example, the system may include an electrosurgical generator arranged to supply microwave energy and radiofrequency energy; and the electrosurgical instrument of the invention connected to receive the microwave energy and radiofrequency energy from the electrosurgical generator. The electrosurgical apparatus may further include a surgical scoping device (e.g. an endoscope) having a flexible insertion cord for insertion into a patient's body, wherein the flexible insertion cord has an instrument channel running along its length, and wherein the electrosurgical instrument is dimensioned to fit within the instrument channel.

In this specification "microwave" may be used broadly to indicate a frequency range of 400 MHz to 100 GHz, but preferably the range 1 GHz to 60 GHz. Preferred spot frequencies for microwave EM energy include: 915 MHz, 2.45 GHz, 3.3 GHz, 5.8 GHz, 10 GHz, 14.5 GHz and 24 GHz. 5.8 GHz may be preferred. In contrast, this specification uses "radiofrequency" or "RF" to indicate a frequency range that is at least three orders of magnitude lower, e.g. up to 300 MHz. Preferably, RF energy has a frequency that is high enough to prevent nerve stimulation (e.g. greater than 10 kHz), and low enough to prevent tissue blanching or thermal spread (e.g. lower than 10 MHz). A preferred frequency range for RF energy may be between 100 kHz and 1 MHz.

Herein, the terms "proximal" and "distal" refer to the ends of the electrosurgical instrument further from and closer to the treatment site, respectively. Thus, in use, the proximal end of the electrosurgical instrument is closer to a generator for providing the RF and/or microwave energy, whereas the distal end is closer to the treatment site, i.e. target tissue in the patient.

The term "conductive" is used herein to mean electrically conductive, unless the context dictates otherwise.

The term "longitudinal" used below refers to the direction along the length of the electrosurgical instrument, parallel to the axis of the coaxial transmission line. The term "inner" means radially closer to the centre (e.g. axis) of the instrument. The term "outer" means radially further from the centre (axis) of the instrument.

The term "electrosurgical" is used in relation an instrument, apparatus or tool which is used during surgery and which utilises microwave and/or radiofrequency electromagnetic (EM) energy.

BRIEF DESCRIPTION OF THE DRAWINGS

Examples of the invention are discussed below with reference to the accompanying drawings, in which.

It should be noted that the embodiments shown in the figures are not drawn to scale.

DETAILED DESCRIPTION

Figure 1:
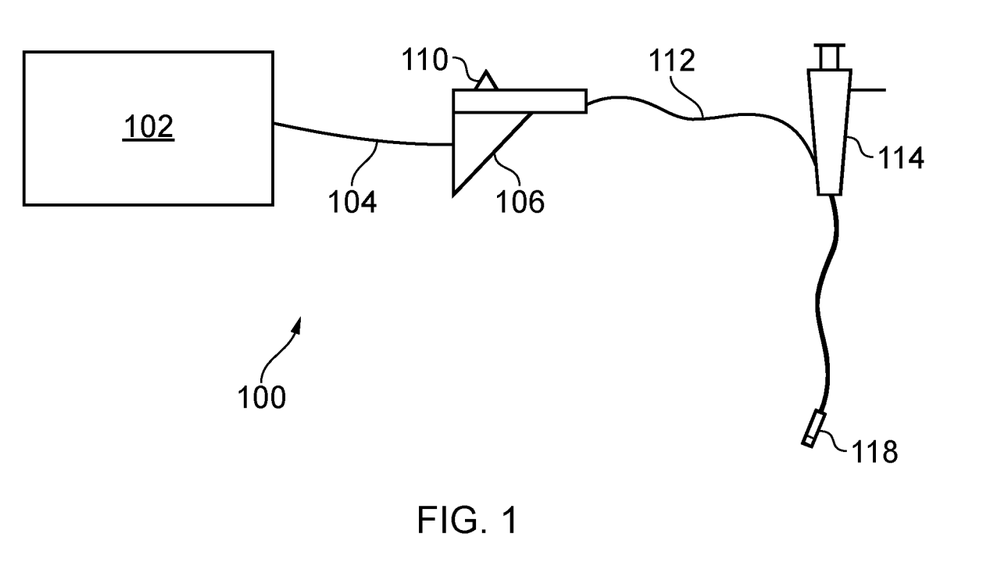
FIG. 1 is a schematic diagram of an electrosurgical system for tissue ablation that is an embodiment of the invention.

FIG. 1 is a schematic diagram of a complete electrosurgical system 100 that is capable of supplying microwave energy and radiofrequency energy to the distal end of a minimally invasive electrosurgical instrument. The system 100 comprises a generator 102 for controllably supplying microwave and radiofrequency energy. A suitable generator for this purpose is described in WO 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level. The generator may be arranged to deliver power in a series of pulses which are modulated to match a patient's breathing cycle. This will allow for power delivery to occur when the lungs are deflated.

The generator 102 is connected to an interface joint 106 by an interface cable 104. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102 and instrument control mechanism into a single flexible shaft 112, which extends from the distal end of the interface joint 106. In other embodiments, other types of input may also be connected to the interface joint 106. For example, in some embodiments a fluid supply may be connected to the interface joint 106, so that fluid may be delivered to the instrument.

The flexible shaft 112 is insertable through the entire length of an instrument (working) channel of an endoscope 114. The flexible shaft 112 has a distal assembly 118 (not drawn to scale in FIG. 1) that is shaped to pass through the instrument channel of the endoscope 114 and protrude (e.g. inside the patient) at the distal end of the endoscope's tube. The distal end assembly includes an active tip for delivering microwave energy and radiofrequency energy into biological tissue. The tip configuration is discussed in more detail below.

The structure of the distal assembly 118 may be arranged to have a maximum outer diameter suitable for passing through the working channel. Typically, the diameter of a working channel in a surgical scoping device such as an endoscope is less than 4.0 mm, e.g. any one of 2.8 mm, 3.2 mm, 3.7 mm, 3.8 mm. The length of the flexible shaft 112 can be equal to or greater than 0.3 m, e.g. 2 m or more. In other examples, the distal assembly 118 may be mounted at the distal end of the flexible shaft 112 after the shaft has been inserted through the working channel (and before the instrument cord is introduced into the patient). Alternatively, the flexible shaft 112 can be inserted into the working channel from the distal end before making its proximal connections. In these arrangements, the distal end assembly 118 can be permitted to have dimensions greater than the working channel of the surgical scoping device 114.

The system described above is one way of introducing the instrument into a patient's body. Other techniques are possible. For example, the instrument may also be inserted using a catheter.

Figure 2:
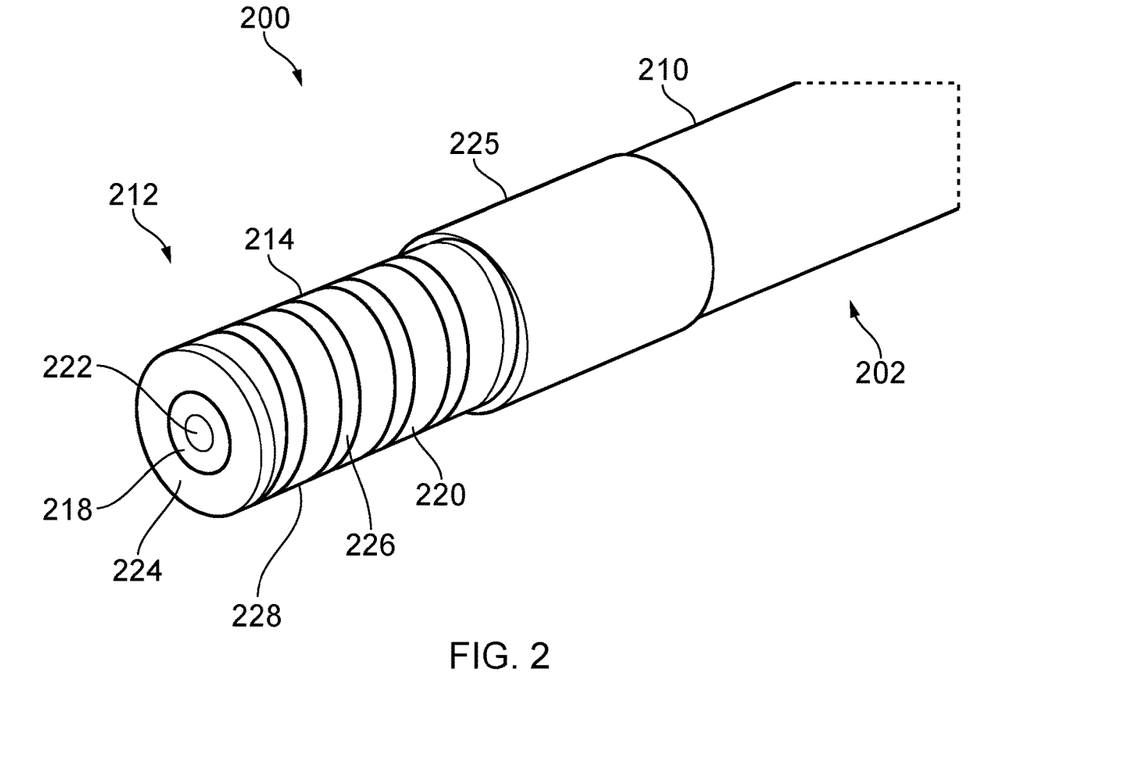
FIG. 2 is a perspective view of an electrosurgical instrument that is an embodiment of the invention.
Figure 3:
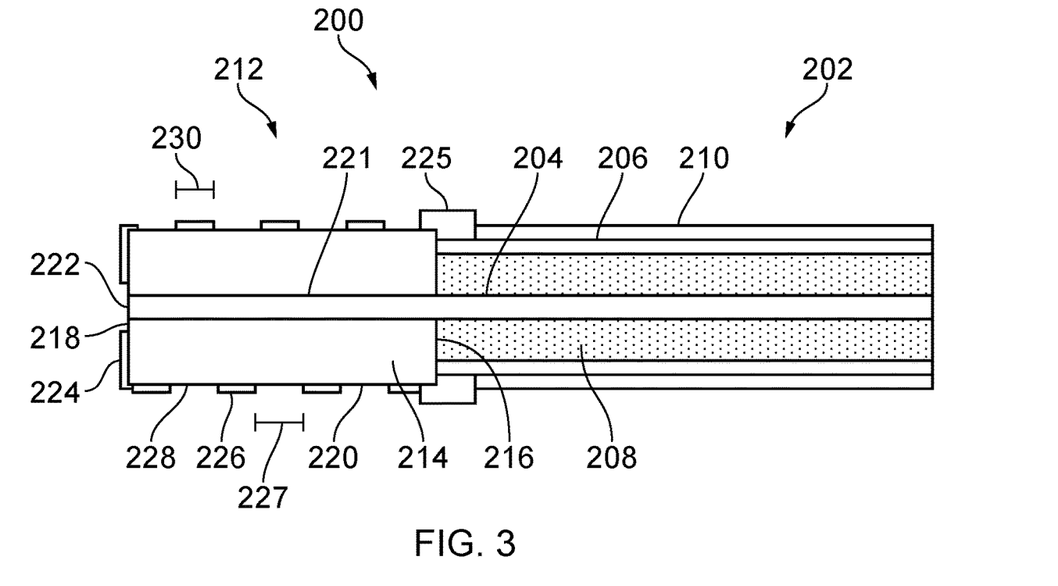
FIG. 3. is a cross-sectional side view of an electrosurgical instrument that is an embodiment of the invention.

FIG. 2 is a perspective view of a distal end of an electrosurgical instrument 200 that is an embodiment of the invention. FIG. 3 shows a cross-sectional side view of the same electrosurgical instrument 200. The distal end of the electrosurgical instrument 200 may correspond, for example, to the distal assembly 118 discussed above. The electrosurgical instrument 200 includes a coaxial feed cable 202 that is connectable at its proximal end to a generator (such as generator 102) in order to convey microwave energy and RF energy. The coaxial feed cable 202 comprises an inner conductor 204 and an outer conductor 206 which are separated by a first dielectric material 208. The coaxial feed cable 202 is preferably low loss for microwave energy. A choke (not shown) may be provided on the coaxial feed cable 204 to inhibit back propagation of microwave energy reflected from the distal end and therefore limit backward heating along the device. The coaxial cable further includes a flexible outer sheath 210 disposed around the outer conductor 206 to protect the coaxial cable. The outer sheath 210 may be made of an insulating material to electrically isolate the outer conductor 206 from its surroundings. The outer sheath 210 may be made of, or coated with, a non-stick material such as PTFE to prevent tissue from sticking to the instrument.

The coaxial feed cable 202 terminates at its distal end with a radiating tip portion 212 for delivering the microwave energy and RF energy conveyed by the coaxial feed cable 202 into biological tissue. The radiating tip portion 212 includes a tip body 214 that is attached to the distal end of the coaxial feed cable 202. The tip body 214 is made of a second dielectric material which may be the same or different from the first dielectric material 208. The second dielectric material may be chosen to improve impedance matching of the radiating tip portion 212 with the target tissue, in order to improve the efficiency of microwave energy delivery into the target tissue. In some examples, the tip body 214 may constitute an extension of the first dielectric material 208 beyond the distal end of the coaxial feed cable 202.

In the example shown, the tip body 214 is cylindrical. It may have substantially the same outer diameter as the coaxial feed cable 202. The dimensions of the tip body 214 may be selected such that is exhibits a desired impedance. A longitudinal axis of the tip body 214 is aligned with a longitudinal axis of a distal portion of the coaxial feed cable 202. The tip body 214 has a proximal face 216, an end face 218 and an outer surface 220, as shown in FIGS. 2 and 3. The proximal face 216 and the end face 218 are at opposite ends of the cylindrical tip body 214. The tip body 214 is attached to the distal end of the coaxial feed cable 202 such that the proximal face 216 of the tip body 214 is in contact with the first dielectric material 208 in the coaxial feed cable 202. The end face 218 of the tip body 214 lies in a plane that is normal to the longitudinal axis of the coaxial feed cable 202. A distal portion 221 of the inner conductor 204 of the coaxial feed cable 202 extends through a channel in the tip body 214. A distal end of the inner conductor 204 is exposed at the end face 218 of the tip body 214, to form a first electrode 222. The first electrode 222 is flush with the end face 216 of the tip body 214. This avoids sharp edges from occurring around the first electrode 222. In the example shown in FIG. 2, the inner conductor 204 has a circular cross-section, so the first electrode 222 has a circular shape. As the central axes of the tip body 214 and the coaxial feed cable 202 are aligned, the first electrode 222 is substantially centred on the end face 218 of the tip body 214.

A second electrode 224 is also disposed on the end face 218 of the tip body 214. The second electrode 214 is ring-shaped, and is arranged such that it encircles the first electrode 222. An outer diameter of the second electrode approximately matches, e.g. extends adjacent or on, the outer diameter of the tip body 214. In one example, the second electrode 224 resembles a conductive cap mounted over a distal end of the tip body 214. The cap may have a short collar extending longitudinally along a distal portion of the outer surface 220 of the tip body. The cap may cover the distal end face of the tip body except for an exposed (e.g. cut or etched away) aperture within which the first electrode 222 is revealed.

The circular first electrode 222 and the ring-shaped second electrode 224 are arranged such that they are concentric. For example, the first electrode 222 may have an outer diameter of approximately 0.5 mm, and the second electrode 224 may have an inner diameter of 1.25 mm. Thus, the first electrode 222 and the second electrode 224 are isolated from one another by a exposed section of the end face 218 of the tip body 214. In the embodiment shown, the end face 218 is flat. However, in other embodiments (not shown), the end face may be rounded or pointed, in order to facilitate insertion into target tissue.

The second electrode 224 is connected to the outer conductor 206 of the coaxial feed cable 202 via a conductive structure that is formed by a helical conductor 226. The helical conductor 226 is disposed on the outer surface 220 of the tip body 214. The helical conductor 226 forms a helix whose central axis is aligned with the longitudinal axis of the tip body 214, such that the helical conductor 226 winds around the outer surface 220 of the tip body 214. Thus, the helical conductor 226 is disposed around the portion of the inner conductor 204 that extends through the channel in the radiating tip portion 212. The helical conductor 226 is isolated from the inner conductor 204 by a radial thickness of the second dielectric material. The helical conductor 226 is connected to the outer conductor 206 via a conductive ring 225 that is disposed at the distal end of the coaxial feed cable 202 and that is electrically connected to the outer conductor 206.

In some examples, the helical conductor 226 may be formed by winding a length of conductive material around the outer surface 220 of the tip body 214, and adhering the conductive material to the tip body 214 (e.g. using an epoxy). In other examples, the helical conductor 226 may be formed by placing a sleeve of conductive material around the outer surface 220 of the tip body 214, and cutting a helical slot in the sleeve of conductive material. In further examples, the helical conductor 226 may constitute an extension of the outer conductor 206 of the coaxial feed cable 202 over the tip body 214, where a helical slot was cut in the portion of outer conductor 206 extending over the tip body 214. In yet further examples, the helical conductor 226 may plated/metalized directly onto the surface of the tip body 214 (e.g. the helical conductor 226 may be formed by depositing and patterning a layer of metal on the tip body 214).

A helical slot 228 is formed between adjacent windings of the helical conductor 226, through which a portion of the outer surface 220 of the tip body 214 is exposed. In other words, the outer surface 220 is exposed between adjacent windings of the helical conductor 226. The pitch of the helical conductor and the width of the helical slot 228 are such that microwave energy that is delivered to the radiating tip portion 212 can escape and radiate outwards. Thus, the radiating tip portion 212 behaves like a slotted (also known as "leaky") coaxial antenna at microwave frequencies. The microwave energy conveyed along the coaxial feed cable 202 may therefore be emitted at the radiating tip portion 212, to deliver microwave energy into target tissue. To enable microwave energy to be emitted from the radiating tip portion 212, the width of the helical slot may be shorter than or equivalent to, the wavelength of the microwave energy. The width of the helical slot 228 is illustrated by line 227 in FIG. 3. Because the helical slot 228 winds all the way around the outer surface 220 of the tip body 214, microwave energy may be emitted uniformly around the outer surface with respect to the central axis of the radiating tip portion 212. Thus, the helical conductor 226 acts as a field-shaping conductive structure for shaping the microwave energy emitted from the radiating tip portion 212.

The radiating tip portion 212 therefore enables microwave emission, whilst maintaining electrical connection to the first and second electrodes 222, 224 on the end face 218 of the tip body 214. The first electrode 222 and the second electrode 224 may be used as bipolar RF electrodes for cutting and/or coagulating tissue using RF energy. For example, the first electrode 222 may act as an active electrode, whilst the second electrode 224 may act as a return electrode for the RF energy. Thus, the radiating tip portion 212 enables treatment of target tissue using both RF and microwave energy: tissue cutting and/or coagulation using RF energy delivered to the first and second electrodes 222, 224; and tissue ablation using microwave energy that is emitted via the "leaky" antenna structure of the radiating tip portion 212.

The location of the first and second electrodes 222, 224 on the end face 218 of the tip body 214 enables the first and second electrodes 222,224 to be used for RF cutting and tunnelling into tissue. By conveying RF energy to the first and second electrodes 222, 224, biological tissue located immediately in front of the radiating tip portion 212 (i.e. tissue that is adjacent to the end face 218) may be cut. Additionally, because the second electrode 224 is formed as a ring around the first electrode 222, tissue may be cut in a region around the first electrode 222. As the tissue in front of the radiating tip portion 212 is cut, it is possible to push the radiating tip portion 212 through the cut tissue and tunnel into a target zone. Because the outer diameter of the second electrode 224 approximately matches the outer diameter of the tip body 214, the cut in the tissue may have approximately the same shape as the cross-section of tip body 214. This may further facilitate tunnelling into the tissue. Then, when the target zone is reached, tissue in the target zone may be ablated by delivering microwave energy into the target zone via the radiating tip portion 212. This enables the radiating tip portion 212 to be placed inside (e.g. near the centre of) a target zone that is to be ablated using microwave energy. For example, using RF cutting, the radiating tip portion 212 may be tunneled into target tissue that is to be ablated (e.g. tissue in the liver, kidneys, muscles or blood), before applying microwave energy. Then, when the radiating tip portion 212 is located inside the target tissue, the target tissue may be ablated by delivering microwave energy to the tissue. In this manner, it is possible to improve the efficiency with which the microwave energy is delivered to the tissue whilst reducing the amount of microwave energy that is delivered to healthy tissue.

The pitch of the helical conductor 226 and width of the helical slot 228 are important for the performance of the radiating tip portion 212. A design trade-off for the radiating tip portion 212 consists of making the helical slot 228 wide enough for microwave emission, but narrow enough to facilitate propagation of RF energy to the first and second electrodes 222, 224. In particular, the smaller the width of the helical conductor (illustrated by line 230 in FIG. 3), the larger the impedance of the helical conductor 226, which may result in large amounts of heat being generated at the radiating tip portion 212 by the RF energy. Another important consideration in the construction of the radiating tip portion 212 is the dielectric breakdown strength of the second dielectric material, and the separation between the first and second electrodes 222, 224. For RF cutting to occur between the first and second electrodes 222, 224, a peak voltage of the RF energy should be sufficient to overcome the breakdown voltage of the air gap or tissue between the electrodes, without causing dielectric breakdown in the second dielectric material. The materials used in the radiating tip portion 212 should also be capable of withstanding high working temperatures, due to the high temperatures caused by RF cutting. Suitable materials for the second dielectric material include MACOR® (dielectric strength of about 45 MV/m), Alumina (dielectric strength of about 23 MV/m) and zirconia.

Figure 4:
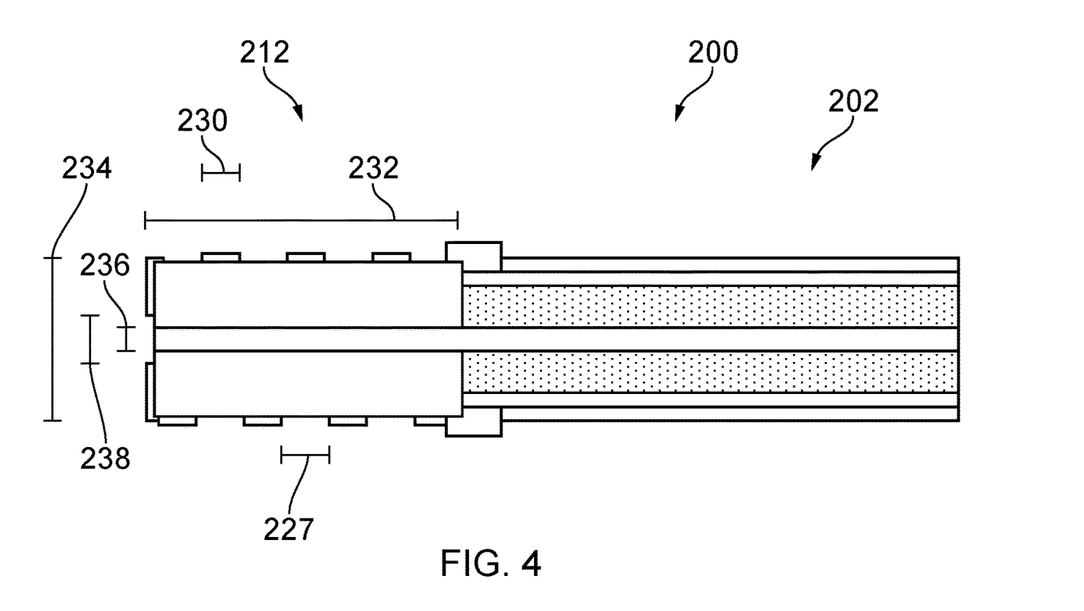
FIG. 4 is a cross-sectional side view of an electrosurgical instrument that is an embodiment of the invention.

FIG. 4 illustrates several of the dimensions of the radiating tip portion 212 of the electrosurgical instrument 200. FIG. 4 shows an identical view of the electrosurgical instrument 200 to FIG. 3, however several of the labels shown in FIG. 3 have been omitted from FIG. 4 for ease of comprehension. The inventors have found that the following are suitable dimensions for the radiating tip portion 212: length of the radiating tip portion 212 in the longitudinal direction (indicated by line labelled with numeral 232): 6 mm; outer diameter of the cylindrical tip body 214 (indicated by line labelled with numeral 234): 2.55 mm; outer diameter of the circular first electrode 222 (indicated by line labelled with numeral 236): 0.5 mm; inner diameter of the ring-shaped second electrode 224 (indicated by line labelled with numeral 238): 1.25 mm; width of helical slot 228 (indicated by line labelled with numeral 227): 1.17 mm; width of helical conductor 226 (indicated by line labelled 230): 0.4 mm. Of course, other dimensions for the radiating tip portion 212 are also possible, and these dimensions are simply given by way of example.

Figure 5A:
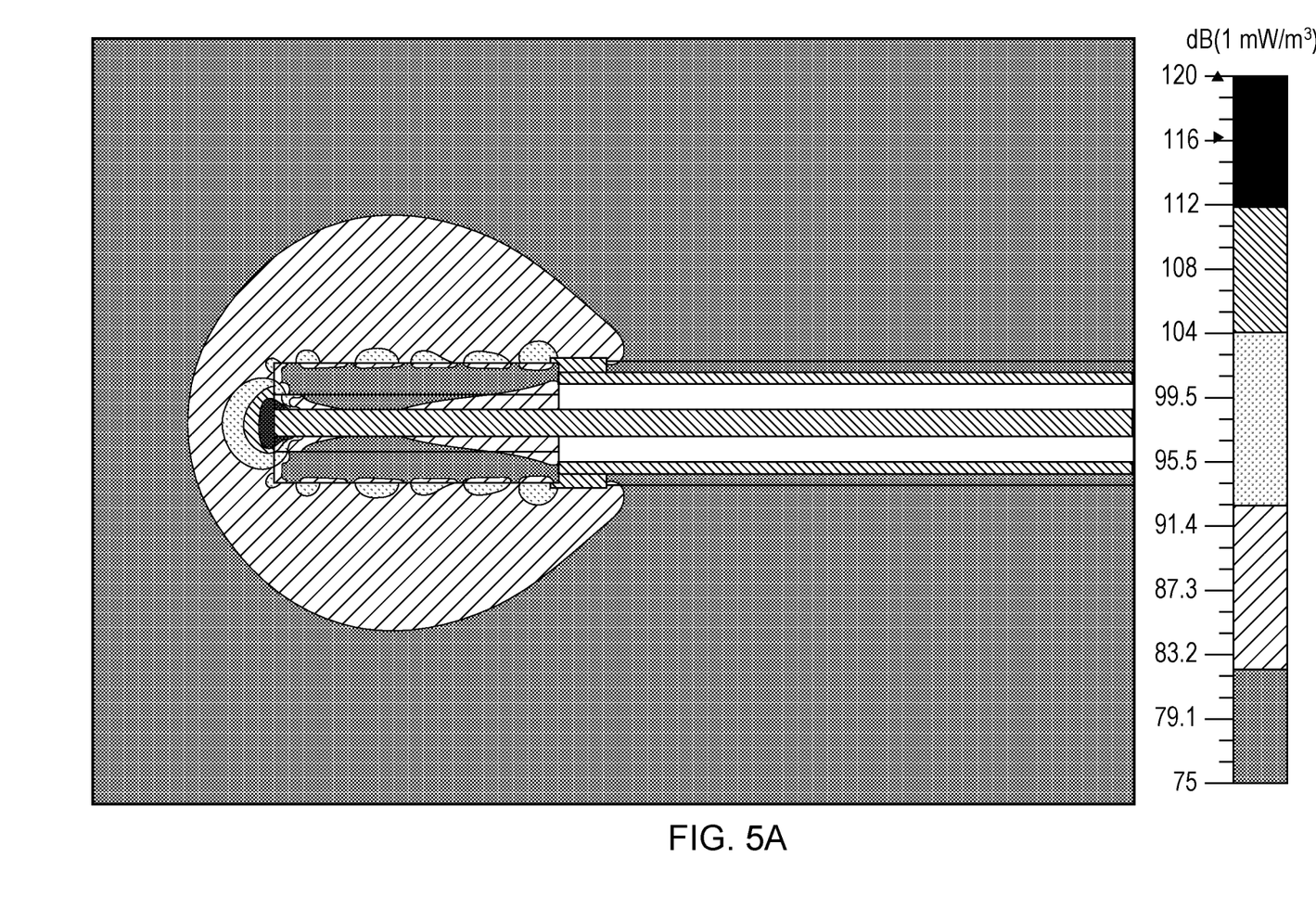
FIGS. 5A and 5B are diagrams showing a simulated microwave radiation profile of an electrosurgical instrument that is an embodiment of the invention.
Figure 5B:
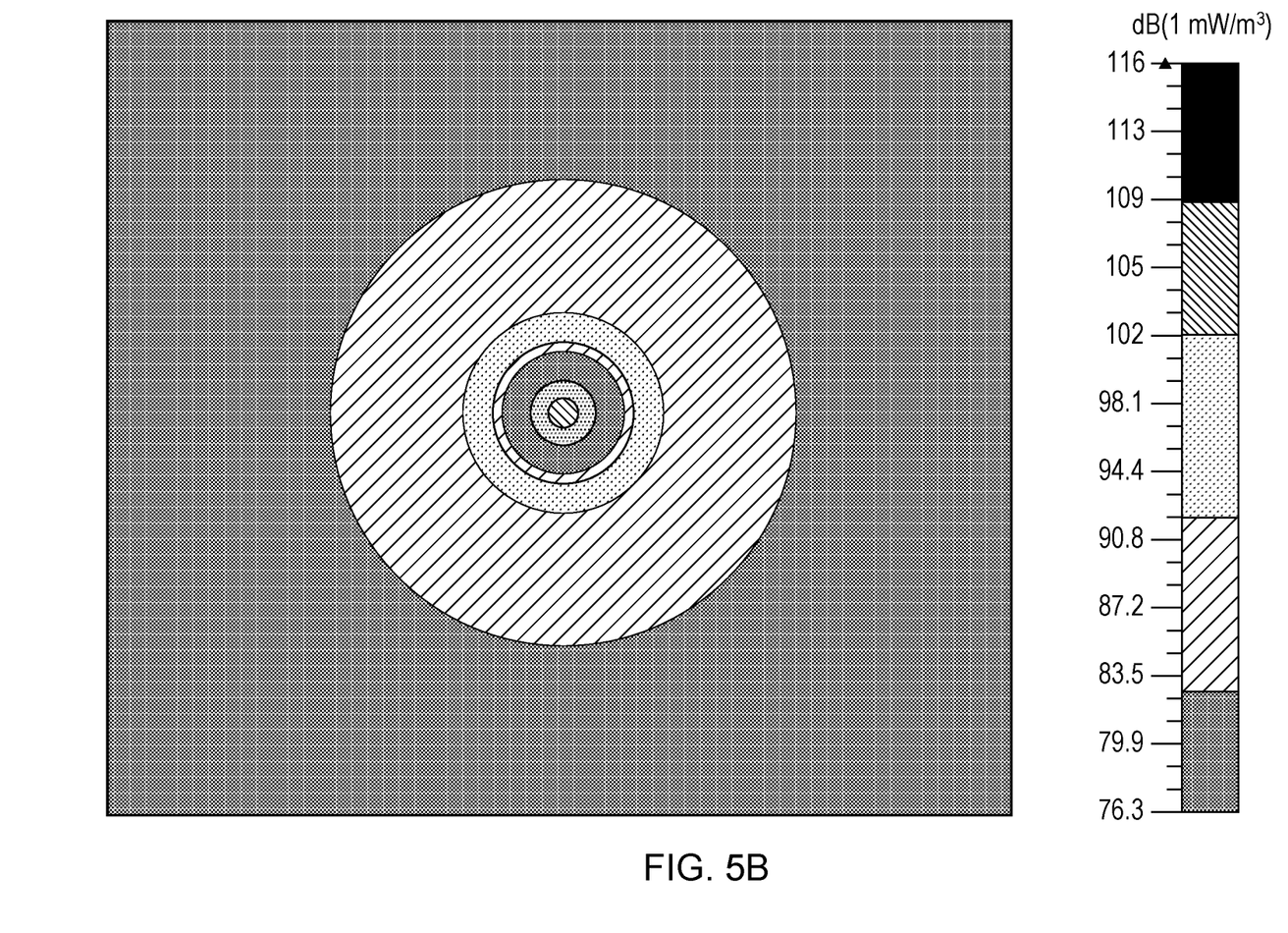

FIG. 5A shows a calculated radiation profile in surrounding tissue for the electrosurgical instrument 200 of FIGS. 2-4 (i.e. with the radiating tip portion 212 having the dimensions discussed above in relation to FIG. 4). The radiation profile was calculated for an EM energy frequency of 5.8 GHz, using finite element analysis. The calculation shows that the microwave energy is radiated from the sides and the distal end of the radiating tip portion 212, i.e. through the helical slot 228. The radiation profile covers an approximately spherical region about the radiating tip portion 212. Thus, the "leaky" antenna structure of the radiating tip portion 212 enables substantially uniform emission of microwave energy about the radiating tip portion 212, so that tissue may be ablated in a well-defined volume about the radiating tip portion 212. FIG. 5B shows an axial cross-section of the calculated radiation profile of FIG. 5A (i.e. FIG. 5B shows the radiation profile in a plane normal to the longitudinal axis of the instrument). As can be seen from FIG. 5B, the radiation profile of the radiating tip portion is substantially symmetrical about the longitudinal axis of the instrument.

Figure 6:
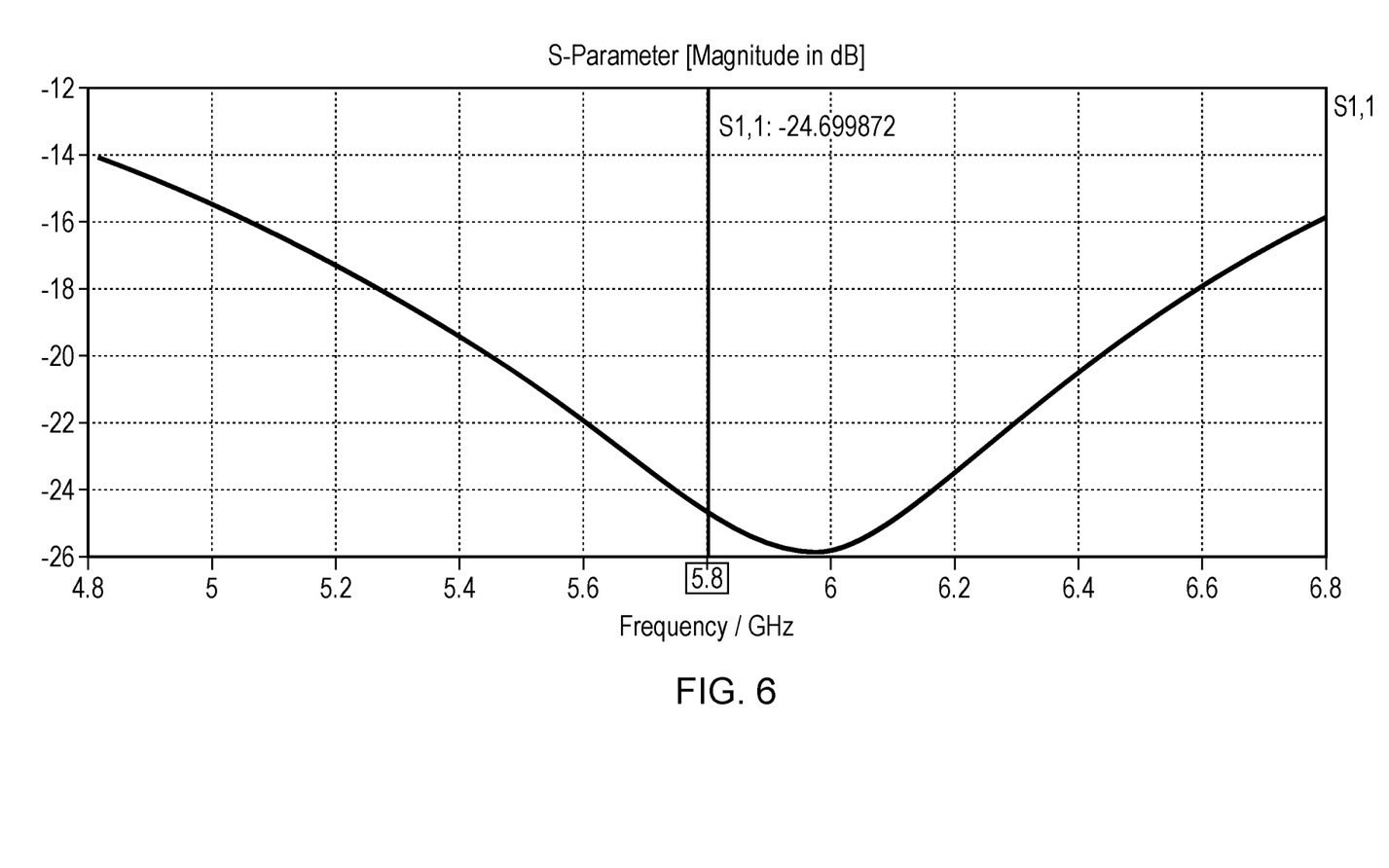
FIG. 6 is a plot of the simulated return loss for an electrosurgical instrument that is an embodiment of the invention.

FIG. 6 shows a simulated plot of the S-parameter (also known as the "return loss") against frequency of the microwave energy for the electrosurgical instrument 200. As well known in the technical field, the S-parameter is a measure of the return loss of microwave energy due to impedance mismatch, and as such the S-parameter is indicative of the degree of impedance mismatch between the target tissue and the radiating tip portion. The S-parameter can be defined by the equation $P_I = SP_R$, where $P_I$ is the outgoing power in the instrument towards the tissue, $P_R$ is the power reflected back from the tissue, and S is the S-parameter. As shown in FIG. 6, the S-parameter is −24.6 dB at 5.8 GHz, meaning that very little microwave energy was reflected back from the tissue at this frequency. This indicates a good impedance match at the operating frequency of 5.8 GHz, and that microwave energy is efficiently delivered from the radiating tip portion into the tissue at this frequency.

Figure 7:
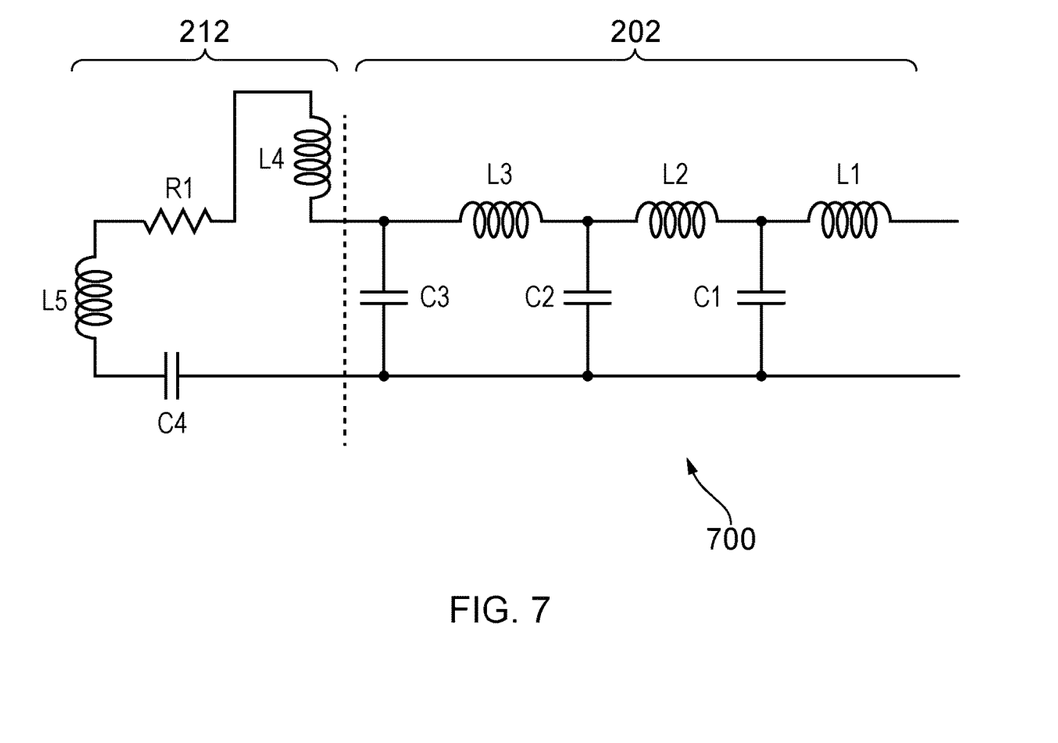
FIG. 7 shows an equivalent circuit diagram for an electrosurgical instrument that is an embodiment of the invention.

FIG. 7 shows a diagram of an equivalent circuit 700 for the electrosurgical instrument 200 of FIGS. 2-4. The coaxial feed cable 202 is represented as an ideal transmission line by inductances L1, L2 and L3, and capacitances C1, C2 and C3. The antenna structure of the radiating tip portion 212 is represented by inductances L4 and L5, resistance R1 and capacitance C4. The helical slot 228 interrupts the current flow path along the outer conductor 206 of the coaxial feed cable 202, and results in an additional inductance. This additional inductance caused by the helical slot 228 is represented by inductance L4 in FIG. 7. The properties of the equivalent circuit 700 may be optimised by controlling the physical properties of the radiating tip portion, e.g. width of helical conductor, tip material, tip dimensions, etc. For example, the width of the helical slot 228 may have an impact on inductance L4. The length or distance of the slot from the coaxial transmission line interface may change the phase of the load and thus the observed impedance. Finite element analysis simulations may be carried out to evaluate the effect of geometry and material changes in the radiating tip portion.

Alternative structures to the one described in the above embodiment are also possible for enabling the treatment of tissue using both RF and microwave energy. In the embodiment described above, the pitch of the helical conductor 226 is constant along the length of the radiating tip portion 212. However, in other examples it is possible for the pitch of the helical conductor to vary along the length of the radiating tip portion. For example, the pitch of the helical conductor may increase (or decrease) towards the distal end of the radiating tip portion. As another example, the helical slot may be tapered along the length of the radiating tip portion, by e.g. increasing or decreasing the width of the helical conductor towards the distal end of the radiating tip portion. Varying the pitch of the helical conductor and/or tapering the helical slot may serve to shape the microwave radiation profile of the radiating tip portion.

In further alternative embodiments, a slotted conductive structure other than a helical conductor may be used to connect the outer conductor of the coaxial feed cable to the second electrode. For example, the second electrode may be connected to the outer conductor via a conductive sleeve that is disposed around the tip body. A series of slots may be cut in the conductive sleeve, to enable microwave energy to be emitted whilst still maintaining an electrical connection to the second electrode. For example, if it is desired to only emit microwave energy in a particular direction, the slots may be provided only on one side of the conductive sleeve.

Figure 8A:
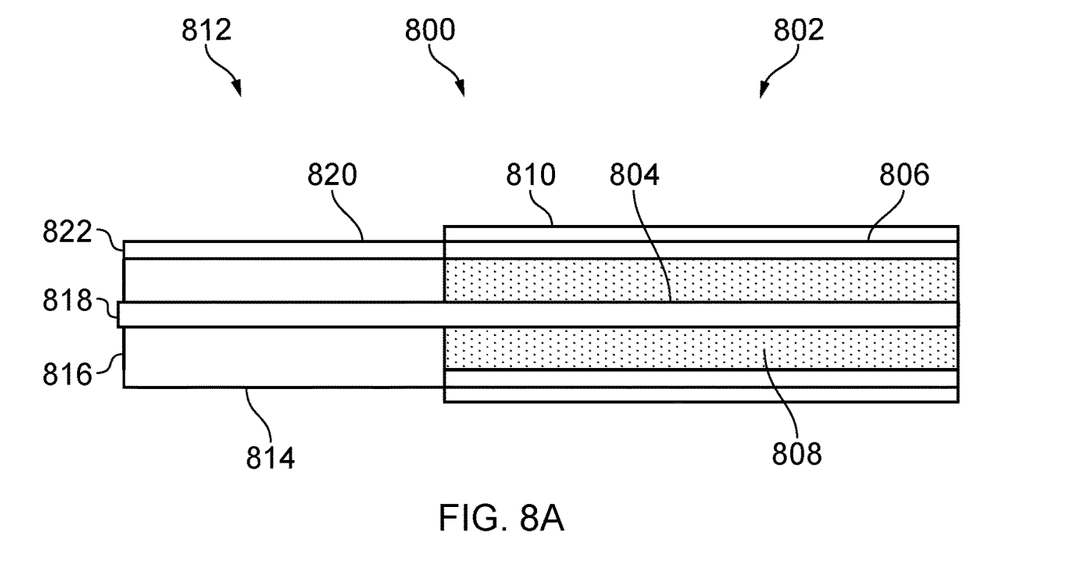
FIG. 8A is a cross-sectional side view of an electrosurgical instrument that is another embodiment of the invention.
Figure 8B:
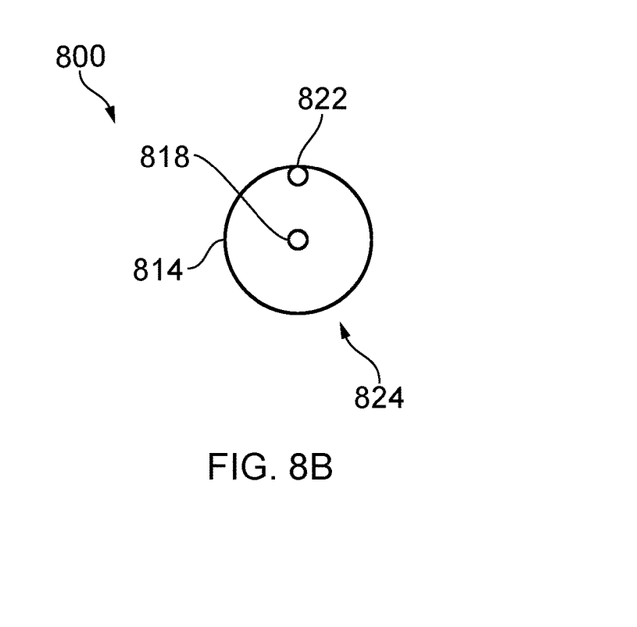
FIG. 8B is a front view of the electrosurgical instrument of FIG. 8A.

FIGS. 8A and 8B illustrate electrosurgical instrument 800, which is another embodiment of the invention. Electrosurgical instrument 800 has a different type of field-shaping conductive structure connecting the outer conductor and the second electrode, compared to electrosurgical instrument 200. FIG. 8A shows a cross-sectional side view of electrosurgical instrument 800, whilst FIG. 8B shows a front view of electrosurgical instrument 800. Electrosurgical instrument 800 includes a coaxial feed cable 802 having an inner conductor 804 and an outer conductor 806 which are separated by a first dielectric material 808. The coaxial feed cable 802 also includes an outer sheath 210. The coaxial feed 802 may be similar to coaxial feed cable 202 of electrosurgical instrument 200.

The coaxial feed cable 802 terminates at its distal end with a radiating tip portion 812. The radiating tip portion 812 includes a tip body 814 that is attached to the distal end of the coaxial feed cable 802. The tip body 814 may be made of a second dielectric material, which may be the same or different from the first dielectric material 808. A portion of the inner conductor 804 extends through a channel in the tip body 814, so that a distal end of the inner conductor is exposed at an end face 816 of the tip body 814. The exposed distal end of the inner conductor 804 forms a first electrode 818 on the end face 816. A wire 820 made of conductive material extends along the length of the radiating tip portion 812, from the distal end of the coaxial cable 802 to the end face 816 of the radiating tip portion 812. The wire 820 is electrically connected at one end to the outer conductor 806. As shown in FIG. 8B, the wire 820 is partially embedded in the tip body 814. A distal end of the wire 820 is exposed at the end face 816 to form a second electrode 822.

As the first and second electrodes 818, 822 are electrically connected to the inner and outer conductors 804, 806, respectively, the may act as RF cutting electrodes (similarly to electrodes 222, 224 of electrosurgical instrument 200). Furthermore, microwave energy delivered to the radiating tip portion 812 from the coaxial feed cable 802 may be emitted by the radiating tip portion 812. However, in contrast to the helical conductor 226 of instrument 200, the wire 820 is disposed only on one side of the radiating tip portion 812 (i.e. it does not wind around the tip body). As a result, the wire 820 will act to partially block microwave energy on one side of the radiating tip portion 814, such that the microwave radiation profile will not be symmetrical about the longitudinal axis of the instrument. Thus, microwave energy may be preferentially emitted from the side of the radiating tip portion 812 that is opposite the wire 820 (e.g. the side indicated by arrow 824 in FIG. 8B). Therefore the wire 820 serves the dual function of connecting the outer conductor 806 to the second electrode 822, and of shaping the microwave radiation profile.

The invention claimed is:

1. An electrosurgical instrument comprising:
   a coaxial feed cable for conveying microwave energy and radiofrequency energy, the coaxial feed cable having an inner conductor, an outer conductor, and a first dielectric material separating the inner conductor and the outer conductor; and
   a radiating tip portion disposed at a distal end of the coaxial cable to receive the microwave energy and the radiofrequency energy, the radiating tip portion comprising:
      a tip body made of a second dielectric material, the tip body having a proximal end that is connected to a distal end of the coaxial feed cable and a distal end facing away from the coaxial feed cable, wherein the tip body includes an end face at the distal end of the tip body; and
      a first electrode and a second electrode disposed on the end face of the tip body, the second electrode being spaced from the first electrode by a portion of exposed second dielectric material,
   wherein the first electrode is electrically connected to the inner conductor of the coaxial feed cable by a conductive element that extends through a channel in the tip body,
   wherein the second electrode is electrically connected to the outer conductor of the coaxial cable by a field-shaping conductive structure formed in or on the tip body,
   wherein the first electrode and second electrode are configured as active and return electrodes for delivering the radiofrequency energy,
   wherein the conductive element and the field-shaping conductive structure are configured as an antenna for emitting the microwave energy,
   wherein the field-shaping conductive structure is configured to shape a radiation profile of microwave energy emitted from the radiating tip portion, and
   wherein the second electrode comprises a conductive cap mounted over the distal end of the tip body, and wherein the cap covers the end face of the tip body except for an exposed aperture within which first electrode is revealed.

2. The electrosurgical instrument according to claim 1, wherein the field-shaping conductive structure includes an elongate conductor extending along a length of the radiating tip portion.

3. The electrosurgical instrument according to claim 1, wherein the field-shaping conductive structure includes a slotted conductive structure formed around the conductive element.

4. The electrosurgical instrument according to claim 3, wherein the slotted conductive structure comprises a helical conductive element wound around an outer surface of the tip body to form a helical slot in which the second dielectric material is exposed.

5. The electrosurgical instrument according to claim 4, wherein a pitch of the helical slot varies along a length of the conductive structure.

6. The electrosurgical instrument according to claim 4, wherein a width of the helical slot tapers as it extends towards or away from the distal end of the tip body.

7. The electrosurgical instrument according to claim 3, wherein the slotted conductive structure comprises a slot having a width that is around a tenth of a wavelength of the microwave energy in biological tissue.

8. The electrosurgical instrument according to claim 3, wherein the slotted conductive structure includes a plurality of slots for emitting the microwave energy.

9. The electrosurgical instrument according to claim 8, wherein each of the plurality of slots has an identical width, and the slots are evenly spaced along a longitudinal direction of the radiating tip portion.

10. The electrosurgical instrument according to claim 8, wherein each of the plurality of slots has a different width, and wherein the plurality of slots are arranged along a longitudinal direction of the radiating tip portion in order of increasing width.

11. The electrosurgical instrument according to claim 3, wherein the slotted conductive structure is formed by an extension of the outer conductor over the tip body.

12. The electrosurgical instrument according to claim 3, wherein the slotted conductive structure is electrically connected to the outer conductor by a conductive ring disposed at the distal end of the coaxial feed cable.

13. The electrosurgical instrument according to claim 1, wherein the conductive element comprises a distal portion of inner conductor that protrudes through the tip body to connect to the first electrode.

14. The electrosurgical instrument according to claim 13, wherein the first electrode is an exposed distal tip of the distal portion of the inner conductor.

15. The electrosurgical instrument according to claim 3, wherein the slotted conductive structure is formed on an outer surface of the tip body.

16. The electrosurgical instrument according to claim 1, wherein the tip body is cylindrical.

17. The electrosurgical instrument according to claim 1, wherein the end face of the tip body lies in a plane that is normal to a longitudinal axis of the coaxial feed cable.

18. The electrosurgical instrument according to claim 1, wherein the end face of the tip body is dome-shaped or conical.

19. The electrosurgical instrument according to claim 1, wherein the second electrode is a conductive ring that surrounds the first electrode.

20. The electrosurgical instrument according to claim 19, wherein an outer diameter of the second electrode is substantially the same as an outer diameter of the tip body.

21. An electrosurgical system comprising:
   an electrosurgical generator arranged to supply microwave energy and radiofrequency energy; and
   an electrosurgical instrument comprising:
      a coaxial feed cable for conveying microwave energy and radiofrequency energy, the coaxial feed cable having an inner conductor, an outer conductor, and a first dielectric material separating the inner conductor and the outer conductor; and
      a radiating tip portion disposed at a distal end of the coaxial cable to receive the microwave energy and the radiofrequency energy, the radiating tip portion comprising:
         a tip body made of a second dielectric material, the tip body having a proximal end that is connected to a distal end of the coaxial feed cable and a distal end facing away from the coaxial feed cable, wherein the tip body includes an end face at the distal end of the tip body; and
         a first electrode and a second electrode disposed on the end face of the tip body, the second electrode being spaced from the first electrode by a portion of exposed second dielectric material, wherein the first electrode is electrically connected to the inner conductor of the coaxial feed cable by a conductive element that extends through a channel in the tip body, wherein the second electrode is electrically connected to the outer conductor of the coaxial cable by a field-shaping conductive structure formed in or on the tip body, wherein the first electrode and second electrode are configured as active and return electrodes for delivering the radiofrequency energy, wherein the conductive element and the field-shaping conductive structure are configured as an antenna for emitting the microwave energy, and wherein the field-shaping conductive structure is configured to shape a radiation profile of microwave energy emitted from the radiating tip portion, wherein the electrosurgical instrument is connected to receive the microwave energy and radiofrequency energy from the electrosurgical generator, and wherein the second electrode comprises a conductive cap mounted over the distal end of the tip body, and wherein the cap covers the end face of the tin body except for an exposed aperture within which first electrode is revealed.

22. The electrosurgical system according to claim 21 further comprising a surgical scoping device having a flexible insertion cord for insertion into a patient's body, wherein the flexible insertion cord has an instrument channel running along its length, and wherein the electrosurgical instrument is dimensioned to fit within the instrument channel.

* * * * *